US00PP08862P

United States Patent [19]

Olij

[11] Patent Number: Plant 8,862

[45] Date of Patent: Aug. 16, 1994

[54] FLORIBUNDA ROSE PLANT NAMED 'OLYTEL'

[75] Inventor: Huibert W. Olij, De Kwakel, Netherlands

[73] Assignee: The Conard-Pyle Company, West Grove, Pa.

[21] Appl. No.: 74,759

[22] Filed: Jun. 10, 1993

[51] Int. Cl.[5] ..... A01H 5/00

[52] U.S. Cl. ..... Plt./22

[58] Field of Search ..... Plt. 22, 11, 12

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive double bicolored blossoms which are long lasting when cut and placed in a vase. The blossoms are light Cardinal Pink suffused with Turk Red on the upper side and light Cream Yellow more or less edged and suffused with light Cardinal Pink on the under side. The plant exhibits vigorous vegetation and exhibits a bushy growth habit. The new variety is well adapted for greenhouse forcing and is particularly well suited for cut flower production. Good resistance to cryptogamic diseases also is exhibited.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Fantasia variety (U.S. Plant Pat. No. 590). The male parent (i.e., the pollen parent) of the new variety was the Vivaldi variety (non-patented in the United States). The parentage of the new variety can be summarized as follows:

FANTASIA×VIVALDI.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive long-lasting bicolored double blossoms which are light Cardinal Pink suffused with Turk Red on the upper side and light Cream Yellow more or less suffused with light Cardinal Pink on the under side,
(b) forms bronze green adult wood,
(c) forms vigorous vegetation,
(d) exhibits a bushy growth habit,
(e) is particularly well suited for forcing and cut flower production in a greenhouse, and
(f) is not particularly affected by cryptogamic diseases.

The new variety undergoes asexual propagation by a number of routes, including budding, grafting, cuttage, etc. The characteristics of the new variety have been found to be strictly transmissible by such asexual propagation from one generation to another in France and in the United States.

The new variety has been named the Olytel variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were one year of age and were observed during February while budded on *Rosa indica* understock and growing in greenhouses at Cap d'Antibes, France.

FIG. 1—illustrates a specimen of a young shoot;

FIG. 2—illustrates a specimen of floral bud with partial opening of the sepals;

FIG. 3—illustrates a specimen of a floral bud at the further opening of the sepals;

FIG. 4—illustrates a specimen of a flower in the course of opening;

FIG. 5—illustrates a specimen of an open flower — plan view — obverse;

FIG. 6—illustrates a specimen of an open flower — plan view — reverse;

FIG. 7—illustrates a specimen of a fully open flower — plan view — obverse;

FIG. 8—illustrates a specimen of a fully open flower — plan view — reverse;

FIG. 9—illustrates a specimen of a floral receptacle showing the arrangement of the stamens and pistils;

FIG. 10—illustrates a specimen of a floral receptacle showing the arrangement of the pistils (stamens removed);

FIG. 11—illustrates a specimen of a flowering stem;

FIG. 12—illustrates a specimen of an adult main branch;

FIG. 13—illustrates a specimen of a leaf with three leaflets — upper surface;

FIG. 14—illustrates a specimen of a leaf with five leaflets — under surface; and FIG. 15—illustrates a specimen of a leaf with seven leaflets — upper surface.

DETAILED DESCRIPTION

Figures 1, 2, 3, 4, 5, 6, 7, 8, 9, 10, 11, 12, 13, 14, 15:
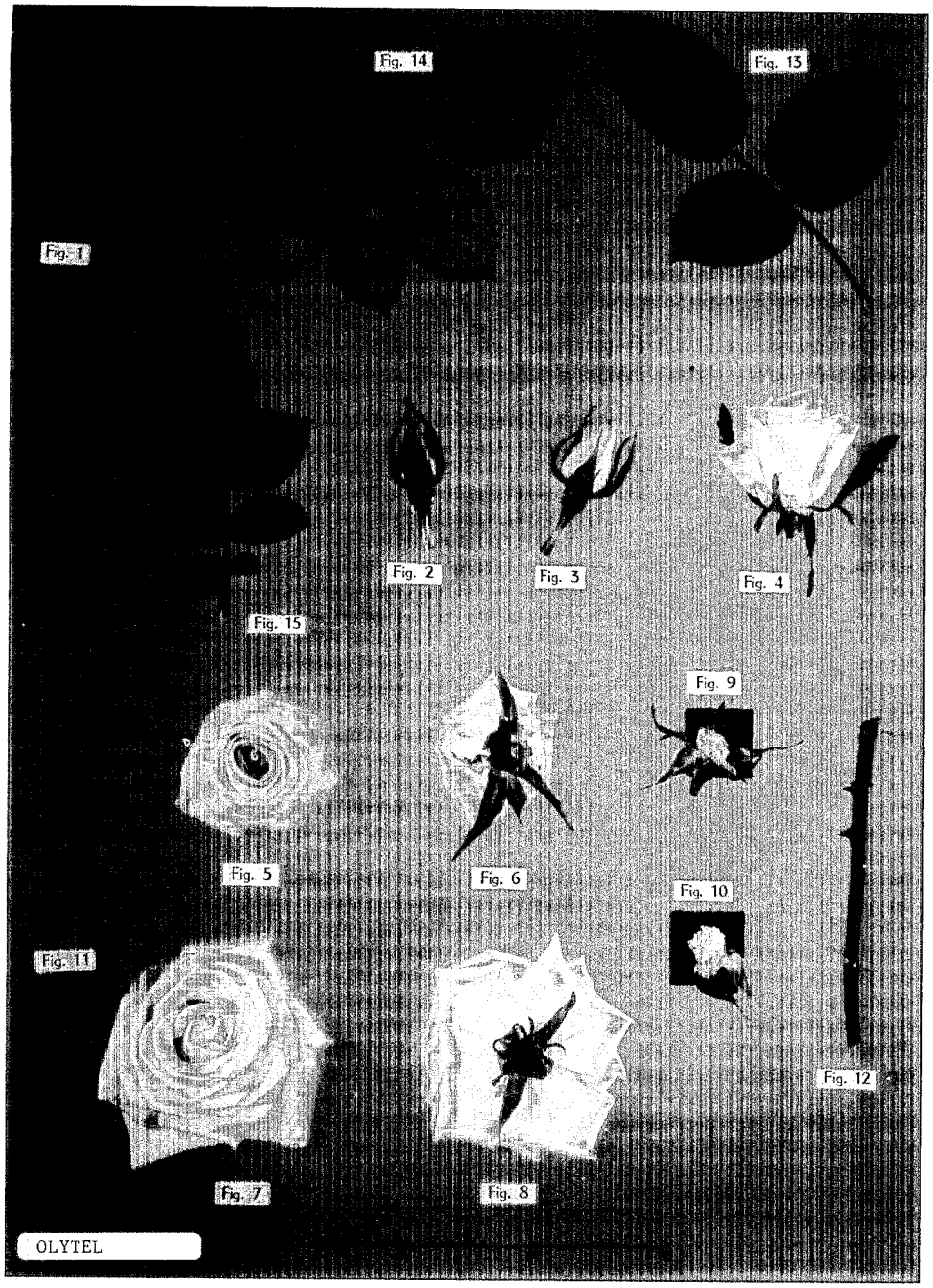

The chart used in the identification of the colors is that of the Royal Horticultural Society (R.H.S. Colour Chart). The terminology which precedes reference to the chart has been added to indicate the corresponding color in more common terms. The description is based on one year old specimens of the new variety during February while budded on *Rosa indica* understock and growing in greenhouses at Cap d'Antibes, France.

Class: Floribunda (Sweetheart).

Plant:

*Height.*—When the plants are cut to a height of 85 cm., the flowering stems commonly measure approximately 30 to 50 cm. When grown in fields at Wasco, Calif., the plants commonly achieve a height of approximately 60 cm. at the end of one growing season.

*Habit.*—Bushy.

Branches:

*Color.*—Young Stems: lettuce green, Yellow-Green Group 144A. Adult wood: bronze green, Yellow-Green Group 146A.

*Thorns.*—Size: small. Quantity: less than average. Color: pinkish on young stems, and greenish-pink on mature wood.

Leaves:

*Stipules.*—Adnate, pectinate, fairly wide and linear.

*Petioles.*—Upper surface: striped reddish brown on young foliage and medium green on mature foliage with more or less glandular edges. Under surface: light green, with a few prickles.

*Leaflets.*—Number: 3, 5 (most often), and 7. Shape: elliptic. Serration: single and regular. Texture: consistent. General appearance: dense and semi-matte foliage. Color (young foliage): Upper surface: medium green, Green Group 137B suffused with dark green, Green Group 139A, and more or less stained with reddish coloration. Under surface: light green, Green Group 139C suffused with grayish-green, Greyed-Green Group 191A. Color (adult foliage): Upper surface: dark green, Green Group 139A. Under surface: Grayish green, Greyish-Green Group 191A.

Inflorescence:

*Number of flowers.*—Usually one bloom per stem.

*Peduncle.*—Light green, somewhat hairy, and approximately 5 to 7 cm. in length on average.

*Sepals.*—Upper surface: tomentose and greenish in coloration. Under surface: medium green, and the outer sepals commonly are slightly appendiculated.

*Buds.*—Shape: conical. Length: approximately 2.5 cm. on average. Size: small. Color upon opening: Upper surface: light Cardinal Pink, Red Group 53C, more or less suffused with Turk Red, Red Group 43C, and dotted with light Sulphur Yellow, Yellow Group 6D. Under surface: light Cream Yellow, Yellow Group 8D, edged and more or less suffused with light Cardinal Pink, Red Group 53C.

*Flower.*—Shape: cup-like, and fully double. Diameter: approximately 8 cm. on average. Color (when opening begins): Upper surface: light Cardinal Pink, Red Group 53C, suffused with Turk Red, Red Group 43C, and dotted with light Sulphur Yellow, Yellow Group 6D. Under surface: light Cream Yellow, Yellow Group 8D, and edged and more or less suffused with light Cardinal Pink, Red Group 53C. Color (when blooming): Upper surface: light Cardinal Pink, Red Group 53C, suffused with Turk Red, Red Group 43C, and dotted with with light Sulphur Yellow, Yellow Group 6D. Under surface: light Cream Yellow, Yellow Group 8D, and edged and more or less suffused with Cardinal Pink, Red Group 53C. Color (at end of opening): Upper surface: light Cardinal Pink, Red Group 53D, suffused with Turk Red, Red Group 43C and dotted with light Sulphur Yellow, Yellow Group 6D. Under surface: light Cream Yellow, Yellow Group 8D, and edged and more or less suffused with light Cardinal Pink, Red Group 53D. Fragrance: slight. Lasting quality: long lasting blossoms when cut and placed in a vase. Petal drop: good. Petal number: approximately 27 to 30 on average. Petal texture: consistent. Stamen number: approximately 92 on average. Anthers: normal and ochre in coloration. Filaments: greenish in coloration and are of irregular heights. Pistils: approximately 84 on average. Stigmas: normal and straw-like. Styles: tomentose near the base, light fuschia in coloration near the tips, usually free standing and of irregular heights. Receptacle: medium green, smooth, and in longitudinal section in the shape of a pitcher at the dehiscence of the anthers.

Development:

*Vegetation.*—Vigorous.

*Blooming.*—Abundant.

*Resistance to diseases.*—Good.

*Aptitude to be forced.*—Very good.

I claim:

1. A new and distinct variety of Floribunda rose plant characterized by the following combination of characteristics:

(a) forms in abundance attractive long-lasting bicolored double blossoms which are light Cardinal Pink suffused with Turk Red on the upper side and light Cream Yellow more or less suffused with light Cardinal Pink on the under side,
(b) forms bronze green adult wood,
(c) forms vigorous vegetation,
(d) exhibits a bushy growth habit,
(e) is particularly well suited for forcing and cut flower production in a greenhouse, and
(f) is not particularly affected by cryptogamic diseases;

substantially as herein show and described.

* * * * *

OLYTEL